United States Patent
Brenner

Patent Number: 5,154,891
Date of Patent: Oct. 13, 1992

[54] LABORATORY APPARATUS FOR SEPARATING SUBSTANCES FROM GAS SAMPLES

[76] Inventor: Karl S. Brenner, 50 Thomas-Mann-Strasse, 6700 Ludwigshafen, Fed. Rep. of Germany

[21] Appl. No.: 606,323

[22] Filed: Oct. 31, 1990

[30] Foreign Application Priority Data

Nov. 8, 1989 [DE] Fed. Rep. of Germany ....... 3937134

[51] Int. Cl.$^5$ ................................................. B01F 7/16
[52] U.S. Cl. ..................................... 422/102; 422/225; 422/231; 422/257; 422/259; 366/102; 366/169; 366/171; 366/174; 366/194; 366/281; 366/331; 366/343
[58] Field of Search ................. 422/99, 101, 102, 225, 422/231, 257, 258, 259; 366/102, 169, 171, 174, 194, 281, 331, 343

[56] References Cited

U.S. PATENT DOCUMENTS

2,254,352  9/1941  Cloud et al. .................... 422/225 X
2,552,260  5/1951  Cooper et al. ..................... 422/231
2,687,948  8/1954  Gregory et al. .................... 422/231

OTHER PUBLICATIONS

Analytische Methoden, Luftanalysen, vol. 1, D. Henschler Verlag VCH, Spezielle Vorbemerkung, vol. 1, Luftanalysen, pp. 3–6.

Primary Examiner—Lynn M. Kummert

[57] ABSTRACT

The laboratory apparatus is used for separating gaseous, liquid and solid substances from gas samples (for example air) to be trace analyzed. It comprises a vessel and a mixer insert with nozzles. The gas fed into the mixer insert emerges from the nozzles at high speed into an absorption liquid held in the vessel so that intensive mixing and hence high absorption of the substances takes place. After passing through the liquid the gas leaves the vessel via an outlet. The substances absorbed in the liquid are available for analysis.

9 Claims, 2 Drawing Sheets

LABORATORY APPARATUS FOR SEPARATING SUBSTANCES FROM GAS SAMPLES

The present invention relates to laboratory apparatus for separating gaseous, liquid and solid substances from gas samples, consisting of a cylindrical vessel, comprising a sleeve and an impingement surface, and of a mixer insert, comprising a core which is insertable into the sleeve, an inlet tube which passes through the core, and an outlet tube.

The prior art way of removing gaseous, liquid, droplet-like and solid particles, ie. aerosols and dusts, from gases, chiefly from air, for analytical determinations involves bringing them into contact with a liquid absorbent (absorption) or with a solid of large surface area (adsorption) in an energy- and time-intensive manner to achieve in this way a transfer from the gas into the absorption or adsorption phase. It is possible to use for this purpose various kinds of wash bottles and adsorption media, such as activated carbon, silica gel, polymer resins and polyurethane foam.

A particular form of absorber using a washing liquid is the laboratory apparatus with mixer insert which is known as an impinger.

In impingers, the gas stream to be analyzed is passed through an appropriately shaped nozzle into the washing liquid in such a way that intensive impingement of the gas stream on the surface of the liquid causes an ultrasonic-type mixing process to occur. As a consequence, mixing is intensive and very finely dispersive. The resulting foam or gas/liquid mixture is backmixed with the bulk of the absorption liquid by the vortices formed with the aid of the feed nozzle. This keeps the carryout of liquid to a minimum. Such apparatus is not only useful for the absorption of gases and aerosols but also for the adsorption of dusts, in particular very fine dusts.

Laboratory apparatus of this type has been described in the relevant literature, for example in Analytische Methoden, Luftanalysen, vol. 1, D. Henschler Verlag VCH (looseleaf collection), under Spezielle Vorbemerkung, Bd. 1 Luftanalysen, pages 3–6.

From experience with the practical use of such apparatus it is known that the effective operating range for the gas flow rate is from 0.5 $m^3$/h to 1.5 $m^3$/h. A figure of 2 $m^3$/h represents the upper limit for the volumetric flow rate through such an arrangement, in particular if two such items of apparatus are connected in series. The optimum flow rate range is from about 1.0 to 1.5 $m^3$/h.

Given the low detection limits required today for certain substances (for example halogenated aromatics, polycyclic hydrocarbons, very fine dusts, etc.), reliable detection and in particular determination require the analysis of such large air or gas volumes that a flow rate of from 1.0 to 1.5 $m^3$/h is too low; that is, taking a sample takes too long for the detection of such a short-lived event, or — when the time required for taking a sample is reasonably short — the detection limit is so high as to rule out any meaningful statement on the basis of the small volumes of collected substance.

The standard demand today of measurements in the environmental, emission control and industrial hygiene sectors requires apparatus capable of higher gas flow rates. Also, the sampling of gas streams containing mixtures of vapors, aerosols and dusts frequently requires the combination of adsorption on solids — in the case of high gas streams preferably on polyurethane foams — and absorption in liquids. Polyurethane adsorbents permit high flow rates, while existing apparatus does not make it possible to achieve a high flow rate for liquid and gas absorption. Increasing the size (diameter) of the nozzle by an appropriate amount does not lead to any improvement. When the nozzle is made larger, the efficiency of mixing is no longer adequate. A broader gas jet displaces the absorption liquid on the impingement plate; true mixing no longer takes place, only an impingement of a gas stream with a subsequent sideways escape, which is more or less what happens in a wash bottle. Also, if the nozzle is too large and the flow rate too high, the pressure imposed on the hardware is so high that in the case of glass vessels, which are necessary in particular for analytical work, the stability of the apparatus and safety are impaired.

It is an object of the present invention to develop an item of laboratory apparatus for separating gaseous, liquid and solid substances from gas samples which permits a significantly higher gas flow rate than existing apparatus, making it possible to collect sufficient gas within a short sampling time for low concentrations of substances to be measured. Furthermore, the new laboratory apparatus should be easy to handle and, having regard to complete detection of trace substances, should be efficiently rinsable.

We have found that this object is achieved by equipping a laboratory apparatus of the type described at the beginning with a plurality of nozzles which communicate with the lower end of the inlet tube via a distributor means.

BRIEF DESCRIPTION OF THE DRAWINGS

Further details and advantages of the novel laboratory apparatus will become apparent from the following description of illustrative embodiments depicted diagrammatically in the drawing, where.

Figure 1:
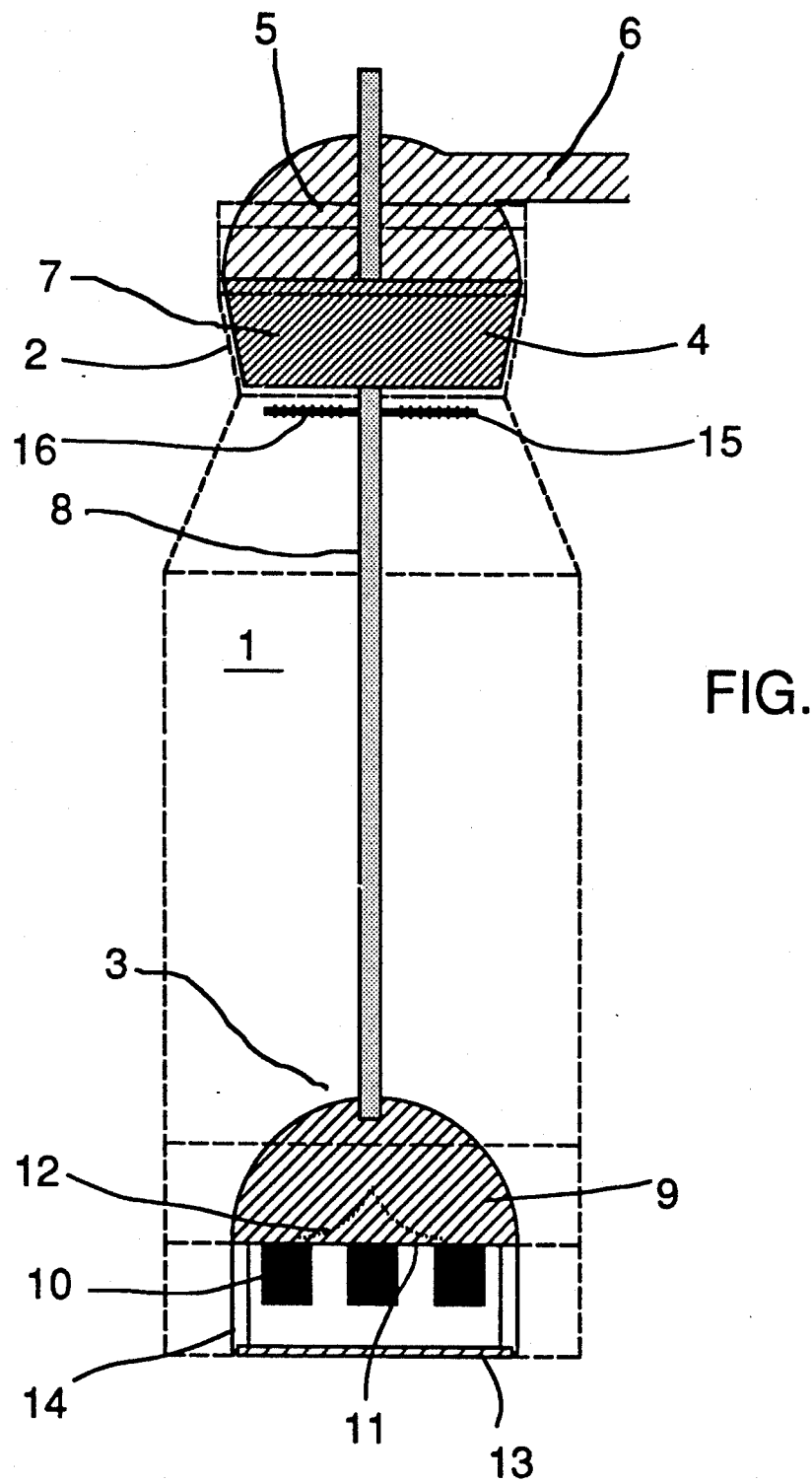
FIG. 1 shows a longitudinal section through a laboratory apparatus with nozzles directed toward the vessel bottom, for static operation.

The laboratory apparatus made of glass (subsequent embodiment) or another inert material, such as a metal or ceramic material, consists of two parts: a cylindrical glass vessel 1 with a ground sleeve 2 at the vessel opening and a mixer insert 3 with a ground core 4 which is insertable into the ground sleeve. Above the ground core is a collecting bell 5 with a lateral outlet tube 6 which communicates with the interior of the glass vessel via perforations 7 in the ground core. To aspirate the gas to be analyzed, an inlet tube 8 passes through the collecting bell 5 and the ground core 4 and ends in the lower part of the glass vessel 1 in the center of a semispheroidal, closed glass bell 9 (FIG. 1). The glass bell acts as a distributor means for nozzles 10 from 2 to 3 mm in size fused into the bell bottom 11 in a uniform arrangement along a circle. It is advantageous to provide above the bell bottom a guide surface 12, for example in the form of a perfectly concavely vaulted cone, to promote in particular the runoff of the absorption liquid when the apparatus is rinsed. The nozzles 10 end about 4 mm above an impingement plate 13 fused to the glass bell 9 by means of glass webs 14.

In a further embodiment not depicted in the drawing, the nozzles 10 may also be arranged at the circumference of the glass bell 9 so that they point in the direction of an impingement surface arranged along the inner circumference of vessel 1.

Before the laboratory apparatus is taken into operation, from 50 to 150 ml of absorption liquid, depending on the particular case, are introduced into the glass vessel 1 and then the mixer inset 3 is inserted. Thereafter the gas or gas mixture to be analyzed, for example air, is aspirated with the aid of a vacuum pump from the take-off point and guided via the inlet tube 8 toward the nozzles 10. The gas emerges from the nozzles at high speed, interacts intensively with the absorption liquid, thereby losing its foreign content, for example aerosols or dusts, and leaves the vessel via the perforations 7, the collecting bell 5 and the outlet tube 6. The mist which occurs in the glass vessel 1 in the course of this process is kept back by a glass plate 15 disposed underneath the ground core 4 and equipped with runoff slots 16.

Following this sampling process, the mixer insert is removed from the glass vessel and rinsed off to recover the deposits of foreign substances, and the material so recovered and the vessel contents are subjected to an analytical determination.

Practical experience with this laboratory apparatus has shown that an arrangement of five nozzles makes possible a gas flow rate of up to 10 m$^3$/h. By increasing the number of nozzles and enlarging the glass vessel it is possible to achieve even higher flow rates. If the absorption of the foreign substances proves difficult, it is advantageous to connect two or more such units of laboratory apparatus in series.

Figure 2:
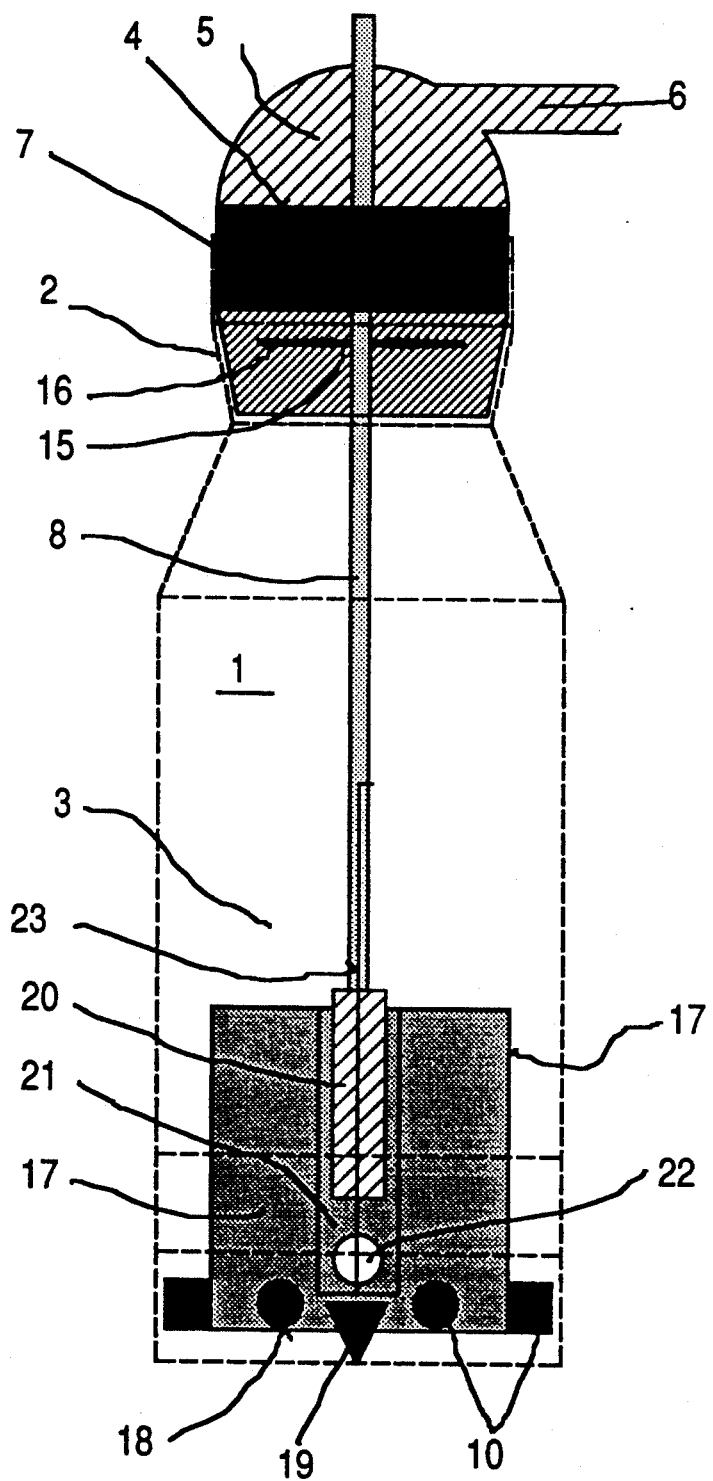
FIG. 2 shows a longitudinal section through a laboratory apparatus with nozzles directed toward the vessel wall, featuring a rotatable nozzle arrangement.

A further embodiment of the laboratory apparatus is shown in FIG. 2 with a rotatable nozzle arrangement. In this embodiment, the distributor means for the aspirated gas comprises a closed glass cylinder 17 rotatably supported at the cylinder bottom 18 by a bearing cone 19 resting on the vessel bottom. The rotatory connection between the fixed inlet tube 8 and the rotatable cylinder is established by a tubular ground core 20 fused to the inlet tube and a ground sleeve 21 integrated into the glass cylinder. The ground sleeve has been provided with at least two mutually opposite communicating openings 22 through which the gas to be analyzed can flow out of the inlet tube 8 and into the glass cylinder 17. Around the lower circumference of the cylinder is a uniform arrangement of nozzles 10, fused into the cylinder wall, which are directed toward the vessel wall and end about 4 mm short of it. A small, unidirectional inclination of the nozzles relative to the cylinder radius sets the glass cylinder into rotation in consequence of the outflowing gas jets. This additionally creates a certain whirling and vortex effect which intensifies the mixing of gas and absorption liquid.

The nozzles 10 can also be fixed to the cylinder bottom instead of the cylinder wall. Similarly it is possible for the above-described glass bell 9 to be made rotatable in the same manner.

It is has been found to be advantageous to provide a holding-down means for the glass cylinder 17, for example in the shape of a glass pin 23 fused into the inlet tube 8 and reaching almost to the bottom of the ground sleeve 21, which prevents the cylinder from being forced upward by buoyancy forces and the bottom of the ground sleeve from coming into frictional contact with the ground core 20.

The laboratory apparatus according to the invention, by virtue of the multiple nozzle arrangement with a variable number of nozzles, makes it possible, compared with existing apparatus, to sample appreciably larger gas volumes over a similar period or previously customary gas volumes within a significantly shorter period. This significantly extends the deployment options for trace analysis.

We claim:

1. Laboratory apparatus for separating a gaseous, liquid or solid substance from a gas sample, consisting essentially of a cylindrical vessel, comprising a sleeve and an impingement surface, a mixer insert comprising a core which is insertable into the sleeve, an inlet tube which passes through the core, and an outlet tube, and a plurality of nozzles which communicate with the lower end of the inlet tube via a distributor means.

2. Laboratory apparatus as claimed in claim 1, wherein the nozzles are disposed a small distance above a bottom side impingement plate.

3. Laboratory apparatus as claimed in claim 1, wherein the nozzles are disposed a small distance away from the inner surface of the vessel.

4. Laboratory apparatus as claimed in claim 1, wherein the distributor means comprises a semispheroidal, closed bell which is connected at a midpoint thereof with the inlet tube and into which the nozzles have been fused.

5. Laboratory apparatus as claimed in claim 4, wherein a guide surface has been arranged within the bell between the nozzles and the midpoint underneath the inlet tube.

6. A laboratory apparatus as defined in claim 5, wherein the bell is rotatably held by means of a bearing cone attached to the bell bottom and resting on the vessel floor, the inlet tube having a tubular core and the bell having a sleeve containing perforations, the core and the sleeve being rotatable relative to one another, and the nozzles being uniformly inclined relative to the axis of rotation.

7. A laboratory apparatus as defined in claim 4, wherein the bell is rotatably held by means of a bearing cone attached to the bell bottom and resting on the vessel floor, the inlet tube having a tubular core and the bell having a sleeve containing perforations, the core and the sleeve being rotatable relative to one another, and the nozzles being uniformly inclined relative to the axis of rotation.

8. Laboratory apparatus as claimed in claim 1, wherein the distributor means comprises a closed cylinder which is connected centrally to the inlet tube and into which the nozzles have been fused.

9. A laboratory apparatus as defined in claim 8, wherein the cylinder is rotatably held by means of a bearing cone attached to the cylinder bottom and resting on the vessel floor, the inlet tube having a tubular core and the cylinder having a sleeve containing perforations, the core and the sleeve being rotatable relative to one another, and the nozzles being uniformly inclined relative to the axis of rotation.

* * * * *